United States Patent
Opremcak

(10) Patent No.: US 7,985,416 B2
(45) Date of Patent: Jul. 26, 2011

(54) BANDAGE AND METHOD FOR VITAL BLEACHING OF SKIN

(76) Inventor: E. Mitchel Opremcak, Delaware, OH (US)

( * ) Notice: Subject to any disclaimer, the term of this patent is extended or adjusted under 35 U.S.C. 154(b) by 249 days.

(21) Appl. No.: 12/535,127

(22) Filed: Aug. 4, 2009

(65) Prior Publication Data

US 2009/0291125 A1    Nov. 26, 2009

Related U.S. Application Data

(60) Division of application No. 11/139,448, filed on May 27, 2005, which is a continuation-in-part of application No. 11/006,215, filed on Dec. 6, 2004, now abandoned.

(51) Int. Cl.
*A61L 15/14* (2006.01)
*A61L 15/08* (2006.01)

(52) U.S. Cl. .......... 424/447; 424/443; 424/445
(58) Field of Classification Search ............... None
See application file for complete search history.

(56) References Cited

U.S. PATENT DOCUMENTS 6,943,197 B2 * 9/2005 Maibach et al. ............. 424/722

\* cited by examiner

*Primary Examiner* — Anand Desai
*Assistant Examiner* — Melissa Mercier
(74) *Attorney, Agent, or Firm* — Roetzel & Andress

(57) ABSTRACT

A bandage and method for vital bleaching of human skin discolored as a result of bruising (ecchymosis) provides transdermal delivery of hydrogen peroxide as a bleaching agent in gel or other form. The bandages provide delivery and application by waterproof and light-proof strips and pads carrying hydrogen peroxide in sufficient concentration for safe oxidation of bruised tissue with resultant eradication of visible discoloration, and amelioration of associated tenderness.

5 Claims, 2 Drawing Sheets

BANDAGE AND METHOD FOR VITAL BLEACHING OF SKIN

CROSS-REFERENCE TO RELATED APPLICATIONS

This application claims priority to and is a divisional application of U.S. patent application Ser. No. 11/139,448 filed on May 27, 2005, which claims priority to and is a continuation-in-part of U.S. patent application Ser. No. 11/006,215 filed on Dec. 6, 2004 now abandoned.

FIELD OF THE INVENTION

The invention is in the general field of dermatology, skin care products and methods of treating skin disorders.

BACKGROUND OF THE INVENTION

Ecchymosis is an area of hemorrhage into the skin and subcutaneous tissue, commonly referred to a bruising. When skin is bruised, it becomes discolored from the escape of blood from ruptured blood vessels into the surrounding tissue to form a purple or black-and-blue spot or area on the skin. This typically occurs in areas where there has been a contusion or similar trauma, and is accompanied by swelling and increased tenderness and pain sensitivity in the region as a result of subcutaneous hemorrhaging. The discoloration can last several days to many weeks, typically affecting areas of the skin that are visible, thus rendering the skin unsightly.

The superficial occurrence of ecchymosis is in most cases not medically significant, and will heal completely in healthy tissue with cellular regeneration of the dermis and removal of red blood cells lying outside the capillaries. As a result of trauma, blood escapes from the vascular tree and accumulates in the tissues. At the earliest stages of onset, ecchymosis presents as a bluish lesion. As the red blood cells in the lesion undergo progressive degeneration and the hemoglobin becomes converted through bilirubin into hemosiderin, the lesion progressively changes in overall color from blue to green to purple and finally to a brownish discoloration. Over time there is infiltration by inflammatory cells, primarily macrophages in which hemosiderin deposition can be seen several weeks to months after the initial lesion. However, the condition is considered by some to be cosmetically significant, particularly to women who would appreciate a safe and effective way to expedite abatement of the unsightly skin discoloration.

Hydrogen peroxide is widely recognized as a highly effective oxidizing agent when used in low concentrations for disinfection, antisepsis and bleaching applications. It is used in very low concentrations, e.g. 3%, for cleaning wounds and removing dead tissue, and is known as an effective cleaning agent for removal of blood stains. Anhydrous solutions of hydrogen peroxide have been used for acne, and bleaching and dyeing of hair. $H_2O_2$ has been proposed for use in various solutions and compositions for skin therapy and wound management, principally for its beneficial oxidative properties, such as disclosed for example in U.S. Pat. Nos. 6,673,374; 6,117,118; 5,879,716; 5,653,994 and 4,826,681. U.S. Pat. No. 6,767,342 discloses a bandage with capsules containing $H_2O_2$ and an adjacent film containing potassium manganate as an oxidation catalyst to promote wound healing. The patent also discloses $H_2O_2$ in layer of gel covered by a release liner proximate to the catalyst.

Combined with urea as carbamide peroxide, in concentrations ranging from about 10% to 20%, it is used in gel form as a tooth whitener. In this application, $H_2O_2$ breaks down into water and oxygen via radical intermediates, able to diffuse through tooth enamel to the dentin and react with polyphenols and other stain pigments in the dentin, at least in part by destroying chromatic double-bond networks of pigment compounds. Most peroxide-containing tooth whiteners in gel form also contain glycerin and carbopol as thickeners and flavoring agents. Stannate and pyrophosphate salts may also be added to scavenge metals and prevent peroxide decomposition during storage. Delivery systems for dental application of carbamide peroxide include formed trays, direct applicators such as brushes, and impregnated strips. The later two rely solely upon the adhesive properties of the gel to keep the $H_2O_2$ in situ.

Apart from $H_2O_2$, U.S. Pat. No. 4,340,590 discloses use of selenium compounds for reduction of ecchymosis in human skin tissue, but does not disclose or suggest any delivery or application system for the described salve or cream formulations.

While the prior art recognizes the use of $H_2O_2$ in various forms as an oxidizing agent for wound care and bleaching applications, it does not address $H_2O_2$ based practical products and methods for eradication of bruising as a cosmetic remedy.

SUMMARY OF THE INVENTION

The invention provides a product and method for vital bleaching of discoloration attendant to ecchymosis, and bandages in various forms adapted for carrying out the method of the invention. The invention includes a bandage for removing the discoloration of skin caused by bruising.

In one embodiment of the invention, a bandage is provided for the vital bleaching of an area of the skin having discoloration as a result of bruising. The bandage includes a material strip with adhesive on one side for removable attachment to skin, a pad of the material strip, a carrier material including a skin bleaching agent on or in the pad, the carrier material containing an amount of hydrogen peroxide ($H_2O_2$) for contact with skin over which the bandage is placed, the amount of hydrogen peroxide in the carrier material sufficient to substantially diminish the discoloration caused by bruising.

One type of skin bleaching agent is in the form of a gel with a hydrogen peroxide component, such as carbamide peroxide. It is also preferred that the concentration of the hydrogen peroxide component of the skin bleaching agent is sufficient to remove the discoloration over a period of time, which period may be less than 24 hours in many cases, particularly those of relatively minor bruising.

It is preferred that the hydrogen peroxide is present in the skin bleaching agent in a concentration of at least about 15% and preferably from about 15% to about 20%, although the invention is not limited to these ranges. Preferably, the gel may be placed on the gauze of a bandage so as to be at least a few millimeters thick.

The method of the present invention includes a method of diminishing coloration of an area of the skin in ecchymosis, the method comprising the steps: (a) providing a bandage adapted to be attached to the skin, the bandage comprising a skin bleaching agent, the carrier material containing an amount of hydrogen peroxide and adapted to release the hydrogen peroxide into the skin over a period of time, the amount of hydrogen peroxide present in sufficient amount so as to substantially diminish the coloration over the period of time; and (b) applying the bandage to the area of skin for sufficient time to substantially diminish or eliminate discoloration of the bruised skin.

DETAILED DESCRIPTION OF PREFERRED AND ALTERNATE EMBODIMENTS

Figure 1:
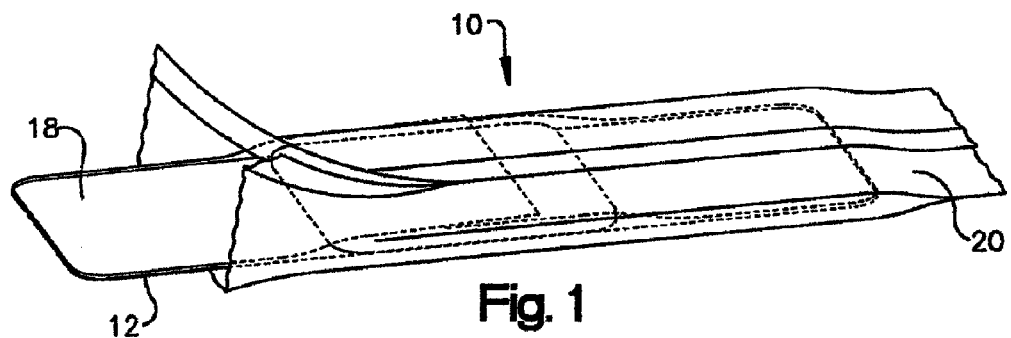
FIG. 1 is a perspective view of a skin bleaching bandage and bandage packaging of the invention.
Figure 2:
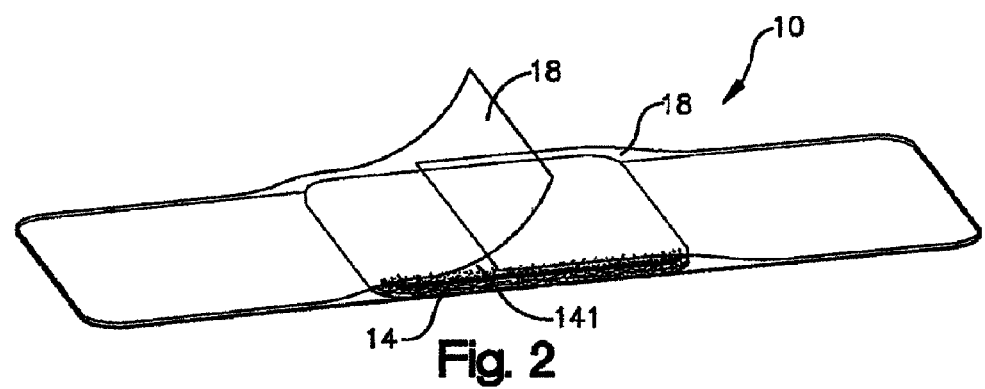
FIG. 2 is a perspective view of a skin bleaching bandage of the invention.

FIG. 1 illustrates one embodiment of a skin bleaching bandage, indicated generally at 10, of the invention. As used and described herein, the terms "skin bleaching bandage" and "bandage" refer to the various combinations of component parts which form a product for skin bleaching and particularly for elimination of bruise marks. As further illustrated in FIGS. 2, 3 and 4, the skin bleaching bandage 10 includes a flexible material layer 12, such as a strip of thin flexible plastic, latex, gauze or woven cloth or non-woven sheet material, which is cut or die-cut to any desired size and shape. The material layer 12 (also referred to herein as a "strip of material" or "cover material") is preferably opaque or otherwise substantially non-transparent to an extent sufficient to block transmission of light of most wavelengths including ultraviolet light which leads to breakdown or degradation of a hydrogen peroxide component, as further described. Water resistant or waterproof properties of the material layer 12 serve to protect the chemical integrity of the skin bleaching agent in contact with bruised skin as further described.

As a generally planar sheet form structure, the flexible material layer 12 has an application side A which is oriented toward the skin when applied, and an exterior side E. Attached to the application side A is a pad 14, which may be in the form of an absorbent fibrous material such as gauze or padding with some bulk or loft intended to substantially cover the affected area of skin, and which occupies a portion or a substantial portion of the application side A of the material layer 12. An adhesive is applied to a portion of remaining portion of the application side A of material layer 12 for temporary adhesion to skin. The adhesive can be of any type and strength suitable for dermatological application as known in the art. For the bandage 10 of the invention, a relatively low or intermediate bonding strength adhesive is suitable, given that for most applications the bandage 10 is not required to remain in place for long periods of time, e.g. exceeding 24 to 48 hours. The pad has one side which is attached to the application side A of the material layer 12, and an opposing skin contact surface 141 oriented for facing contact with skin when the bandage 10 is applied.

A skin bleaching agent 16 is applied to an application side 141 of pad 14, or to the skin contact surface 141 of pad 14 of the bandage 10. Alternatively, the pad 14 is substantially impregnated with the skin bleaching agent 16. One type of skin bleaching agent 16 which is effective in removing the discoloration caused by bruising includes hydrogen peroxide ($H_2O_2$) as an active ingredient. In one embodiment of the invention, the active component of the skin bleaching agent 16 is carbamide peroxide, in gel form, such as for example 5% to 30% carbamide peroxide and a gel admixture. Carbamide peroxide as an oxidizing agent of the type widely used in gel form for tooth whitening is in concentrations in the approximate range of 5% to 20%, representing approximately 30% $H_2O_2$, which has been discovered by the inventor to be an effective concentration and form for cosmetic removal of superficial bruising. As the active bleaching agent ingredient, approximately 30% hydrogen peroxide concentration breaks down to release oxygen into the tissue plasma resulting in oxidation of loose blood cells visible through the epithelium.

The skin bleaching agent 16 containing $H_2O_2$ can be formulated as a gel, such as an aqueous, alcohol or oil gel with suitable gelling agents, including but not limited to natural gums, acrylic acid and acrylate polymers and copolymers, and cellulose derivatives (e.g., hydroxymethyl cellulose and hydroxypropyl cellulose), and oil gelling agents including but not limited to hydrogenated butylenes/ethylene/styrene copolymer and hydrogenated ethylene/propylene/styrene copolymers. Such gels of poly (vinyl alcohol), known as "hydrated PVA gels", can be used as the base matrix for gels as a delivery/application component of the skin bleaching agent 16. The skin bleaching agent 16 can be in another form essentially a transdermal therapeutic composition which includes hydrated gels of poly (vinyl alcohol) containing $H_2O_2$ as an active bleaching/anti-oxidant substance, and further including pharmacologically active substances and absorption enhancers for the active substances and/or tackifiers.

Also within the scope of the invention is the use of hydrogen peroxide in other forms, concentrations and in combination with other types of carrier materials or admixtures, either impregnated in the pad 14 or distributed over the skin contact surface 141 of the pad 14. The skin bleaching agent 16 may be pre-applied to the skin contact surface 141 of the pad 14 in the manufacture of the bandages 10, or applied by a user to the pad 14 or directly to a bruise and the bandage then applied to cover the affected area. A release liner 18 can be included to cover the pad 14 and skin bleaching agent 16 thereon or therein, and to further maintain sterility of both the pad 14 and skin bleaching agent 16 and prevent migration of the skin bleaching agent 16 from the pad 14 prior to application, and further to prevent environmental degradation of the skin bleaching agent 16 prior to application to a bruise.

Figure 3:
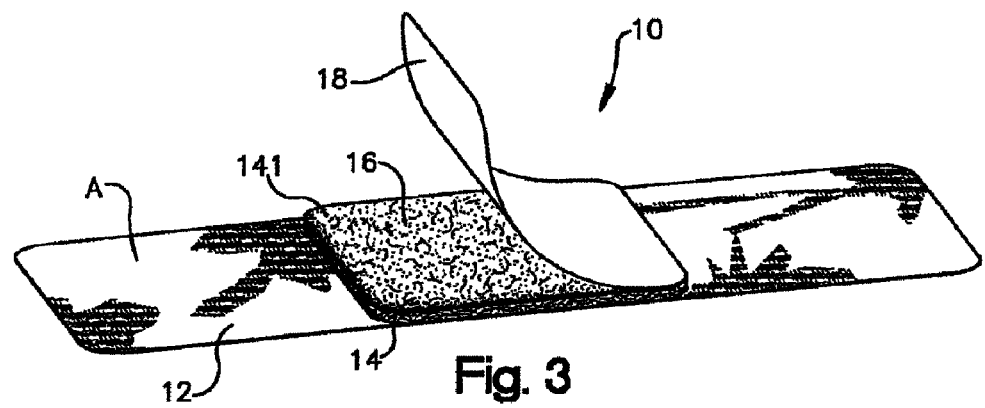
FIG. 3 is a perspective view of an alternate embodiment of a skin bleaching bandage of the invention.
Figure 4:
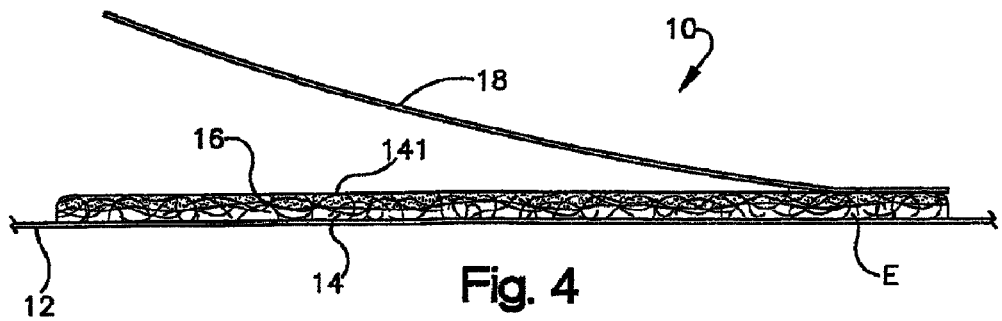
FIG. 4 is a profile view of a skin bleaching bandage of the invention.

As illustrated in FIG. 1, the bandage 10 can be fully enclosed in a package 20, such as a sealed envelope made of cellophane or other plastic or paper material including glassine-type paper, which is preferably solid, opaque or otherwise non-transparent and light-blocking to preserve stability of the skin bleaching agent 16 and provide sterile containment of the bandage 10. The bandage 10 is so packaged in a sterile condition as may be achieved by any appropriate sterilization technique, or alternatively produced in a sterile condition and then packaged in an aseptic manner. For example, individual sterile bandages 10 of common or dissimilar sizes and shapes, with or without package 20, may be grouped together in a container such as a box which is sealed in a sterile condition. Furthermore, the release liner 18 can serve as a primary sterile barrier at least in part by adhesion to the application side A of the sheet material 12 as shown in FIG. 3, and covering the skin bleaching agent 16 on the skin contact surface 141 of the pad 14 so that the skin bleaching agent 16 is placed into direct contact with the affected area of skin when the bandage 10 is applied. Appropriate methods of sterilization and packaging known in the art include gamma radiation, electron beam, ethylene oxide and like methods of sterilization. Packaging 20 may alternatively be in the form of metallic foil pouches such as aluminum, polyethylene film, ethylene vinyl acetate film, polypropylene film, polyvinyl chloride film or similar packaging known in the art.

Figure 5:
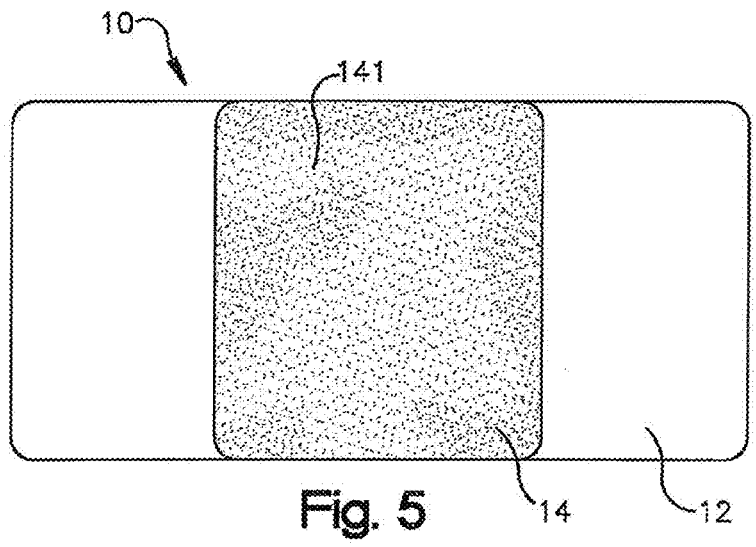
FIGS. 5, 6 and 7 are plan views of alternate embodiments of skin bleaching bandages of the invention.
Figure 6:
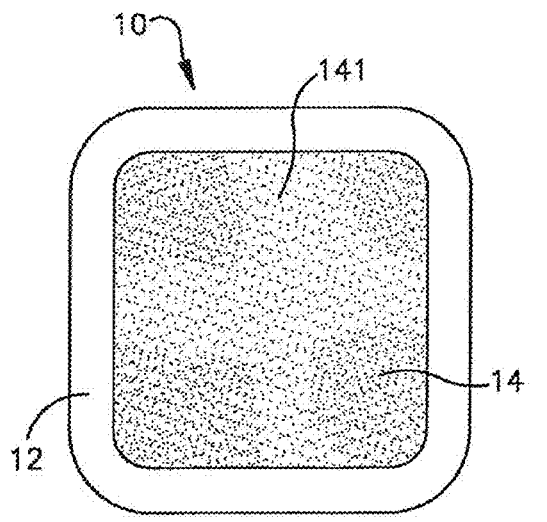
Figure 7:
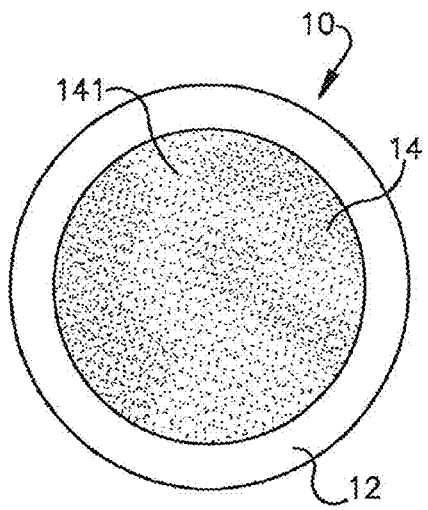

FIGS. 5, 6 and 7 illustrate alternate embodiments of the bandage 10 of the invention wherein the cover material 12 and pad 14 are made in various shapes and sizes to facilitate application and coverage of bruises of different sizes and on different parts of the body. Also apparent from these embodiments is the placement and size of the pad 14 relative to the cover material 12, which in some embodiments can extend beyond one or more edges of the pad 14, or beyond the perimeter of the pad 14 to effectively seal, form light and moisture, the pad (and the skin bleaching agent 16 thereon) against the area of skin to be treated.

In the method of the invention, the skin contact surface 141 of the pad 14 of the bandage 10 is placed in direct contact with a bruised area of the skin, with the adhesive on the application side A of the sheet material 12 bonded to skin proximate to or surrounding the bruised area, and left in place of any period of time sufficient for the oxidation reaction of the hydrogen peroxide with the bruised tissue to occur, which time will vary according to such variables as skin type and condition, extent of injury, ambient atmosphere, so that application times may range anywhere from a few hours to days for visible results to occur.

In the practice of a method of the invention, the skin contact surface 141 of pad 14 of a bandage 10 is coated and/or saturated with 20% hydrogen peroxide gel, applied to one or more bruised areas of the skin, and left in place for a period of 24 hours. The skin bleaching agent 16 is active and effective upon contact with skin, requiring no catalyst or migration out of the pad 14 as there is skin bleaching agent 16 present at the skin contact surface 141 even in those embodiments where the pad 14 is impregnated with the skin bleaching agent 16. There is no discomfort associated with the treatment. Upon removal the area directly under the pad 14 of the applied bandage 10 appears decolorized and white. Bruised skin adjacent to the bandage (not in contact with the skin bleaching agent 16) remains black and blue in color. Importantly the tenderness associated with the two treated bruises was much improved compared to the untreated bruises. The effect was permanent over a period of days the area of bruising immediately adjacent to the treated area decolorized in a delayed fashion but much faster than untreated bruises.

Other materials may be included in the composition, including but not limited to humectants, proteins and polypeptides, preservatives, alkaline agents, chelating agents such as EDTA and preservatives such as parabens. Other constituent elements of the composition may include cosmetic adjuvants, such as dyes, opacifiers (e.g. titanium dioxide), pigments and fragrances. Compositions and formulations containing such compositions may be prepared by conventional methods known in the art.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of diminishing coloration of an area of bruised, unbroken skin, the method comprising the steps:
    obtaining a bandage adapted to be attached to the skin and having an application side, an exterior side, and a pad attached to the application side;
    applying to the pad a skin bleaching agent selective for extra-vascular hemoglobin and red blood cells containing a safe and effective amount of hydrogen peroxide to bleach discoloration from bruised, unbroken skin; and
    applying the bandage to a bruised, unbroken area of skin by attachment of the cover material proximate to the bruised area for a sufficient period of time to allow the agent to selectively lyse extra-vascular hemoglobin and red blood cells, substantially diminishing discoloration from bruising.

2. The method of claim 1, wherein the step of applying the skin bleaching agent to the pad is performed in a bandage manufacturing process.

3. The method of claim 1, wherein the step of applying the skin bleaching agent to the pad is performed by dispensing the skin bleaching agent on to a surface of the pad.

4. The method of claim 1, wherein the step of applying the skin bleaching agent to the pad is performed by impregnating the pad with the skin bleaching agent.

5. The method of claim 1, further comprising the step of forming a package about the bandage.

* * * * *